United States Patent

Maciel et al.

Patent Number: 5,253,539
Date of Patent: Oct. 19, 1993

[54] ANALYZER SYSTEM

[75] Inventors: Robert F. Maciel, Tyngsboro; Bruno De Gironimo, Billerica, both of Mass.

[73] Assignee: Iniziative Marittime 1991, s.r.l., Turin, Italy

[21] Appl. No.: 727,571

[22] Filed: Jul. 9, 1991

[51] Int. Cl.$^5$ ............................................. G01N 21/27
[52] U.S. Cl. .............................. 73/864.83; 73/863.73; 204/409
[58] Field of Search ........... 73/863.72, 863.73, 863.71, 73/864.83, 864.84, 1 G, 1 R; 204/409; 422/103; 251/309, 312; 137/625.47

[56] References Cited

U.S. PATENT DOCUMENTS

| | | | |
|---|---|---|---|
| 2,856,150 | 10/1958 | McDonald | 73/863.73 |
| 4,222,412 | 9/1980 | Carle | 73/864.84 |
| 4,298,026 | 11/1981 | Ambers | 137/625.47 |
| 4,361,539 | 11/1982 | Weinberg | 422/68 |
| 4,535,522 | 8/1985 | Averill | 29/280 |
| 4,909,933 | 3/1990 | Carter et al. | 137/625.47 X |
| 5,154,396 | 10/1992 | Conley et al. | 251/309 |

Primary Examiner—Tom Noland
Attorney, Agent, or Firm—Fish & Richardson

[57] ABSTRACT

An electrochemical analysis system includes a plurality of flow through analysis chambers and a valve connected in series between the outlet port of one analysis chamber and the inlet port of a second analysis chamber and has a first position connecting the two analysis chambers in series for flow of a sample to be analyzed therethrough and a second position in which the two analysis chambers are connected to separate sources of calibrating fluids. The valve includes a housing member with a recess in which a valve spool member is disposed. The spool member includes an array of ports in its cylindrical surface, two ports being interconnected by a through passage, and other ports being separately connected to individual sources of calibrating fluids. The valve spool is centered in the housing recess by a sleeve member that carries an annular seal member that has a continuous annular seal surface in sealing engagement with the cylindrical surface of the valve spool member and through passages that are in fixed alignment with the ports of the housing member.

13 Claims, 2 Drawing Sheets

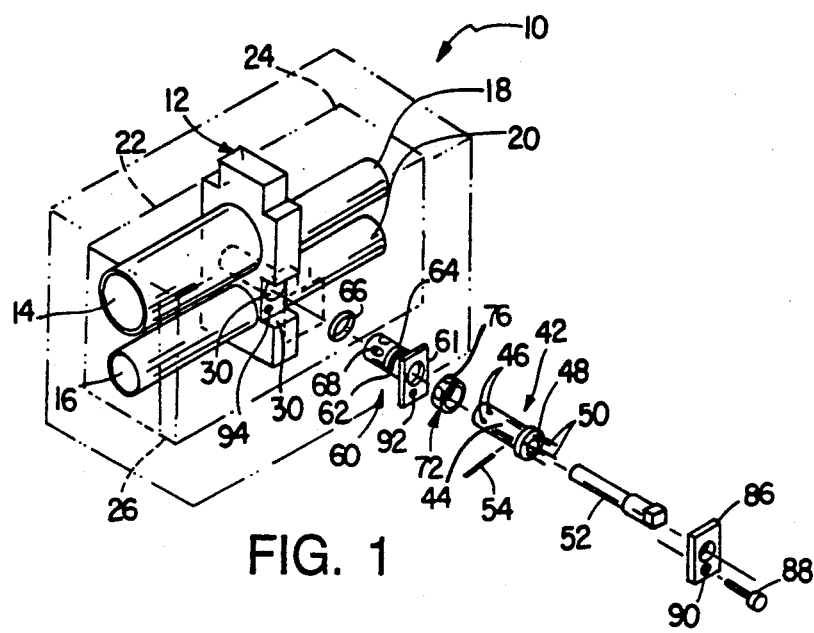
FIG. 1
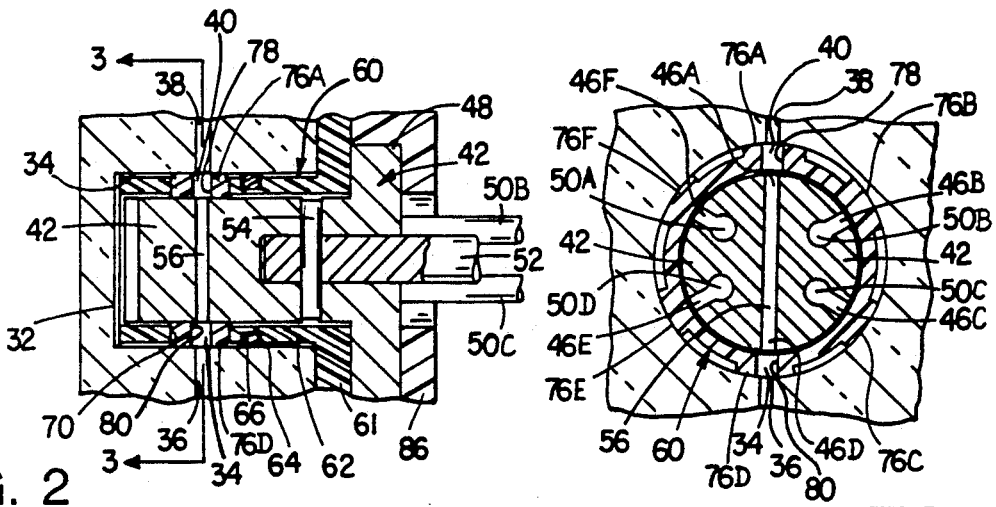
FIG. 2
FIG. 3
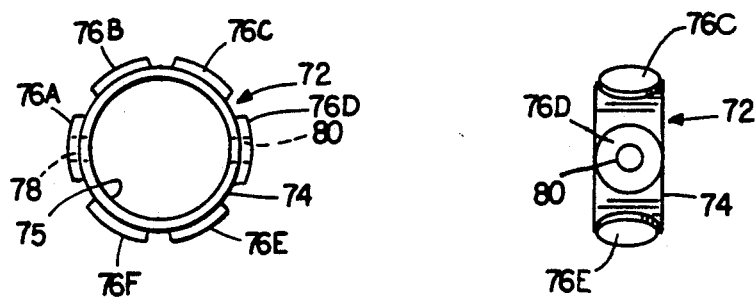
FIG. 4
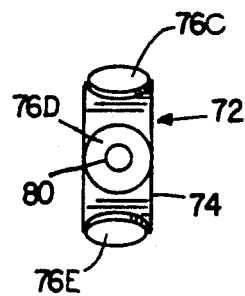
FIG. 5

ANALYZER SYSTEM

BACKGROUND OF THE INVENTION

This invention relates to analyzer systems, and more particularly to valve arrangements that have particular application in analyzer systems for analyzing parameters of biological fluids such as blood.

A blood gas analysis system of the type shown in Weinberg et al. U.S. Pat. No. 4,361,539 includes a module which houses a thermally-insulated integrated assembly with external electrical and fluid connections. That assembly includes, as an integrated unit, four electrode housings between which is disposed a precision flow through cell, two metal heater block assemblies with electrical heater pads for maintaining stable analysis temperature. Located centrally within the flow through cell is a spool valve assembly of the type shown in Ambers U.S. Pat. No. 4,298,026. That valve assembly cooperates with the electrode systems to selectively interconnect sample flow and calibrating fluid flow paths. In that valve, leakage has occurred when the spool valve is moved between positions, allowing sample material to be analyzed to travel along the surface of the valve spool and contact grounded portions of the valve assembly, creating instability and errors in the data measurements as well as interfering with valve operation.

SUMMARY OF THE INVENTION

In accordance with the invention, there is provided an improved valve that has particular application in an electrochemical analysis system that includes a plurality of flow through analysis chambers. In that system, the valve is connected in series between the outlet port of one analysis chamber and the inlet port of a second analysis chamber and has a first position connecting the two analysis chambers in series for flow of a sample to be analyzed therethrough and a second position in which the two analysis chambers are connected to separate sources of calibrating fluids. The valve includes a housing member with a recess in which a valve spool member is disposed. The spool member includes an array of ports in its cylindrical surface, two ports being interconnected by a through passage, and other ports being separately connected to individual sources of calibrating fluids. The housing and spool members include coaxial cylindrical valve surfaces in juxtaposed spaced relation. Formed in the housing member are a plurality of passages, each of which terminates at a port in the cylindrical interior surface. The valve spool is centered in the housing recess by a sleeve member that carries an annular seal member that has a continuous annular seal surface in sealing engagement with the cylindrical surface of the valve spool member and through passages that are in fixed alignment with the ports of the housing member. Preferably, the sleeve member includes apertures in alignment with the annular seal member and portions of the annular seal member protrude through those apertures to provide resilient spaced support of the sleeve member in the housing cavity.

BRIEF DESCRIPTION OF THE DRAWING FIGURES

Other features and advantages of the invention will be seen as the following description of a particular embodiment progresses, in conjunction with the drawings, in which:

FIG. 1 is an exploded perspective view of a blood gas analysis module for use in a blood gas analysis system;

FIG. 2 is a sectional view through the valve assembly employed in the module shown in FIG. 1;

FIG. 3 is a sectional view taken along the line 3—3 of FIG. 2;

FIG. 4 is an elevational view of the seal member employed in the valve assembly shown in FIGS. 2 and 3;

FIG. 5 is an end elevational view of the seal member shown in FIG. 4 and

DESCRIPTION OF PARTICULAR EMBODIMENTS

Figure 6:
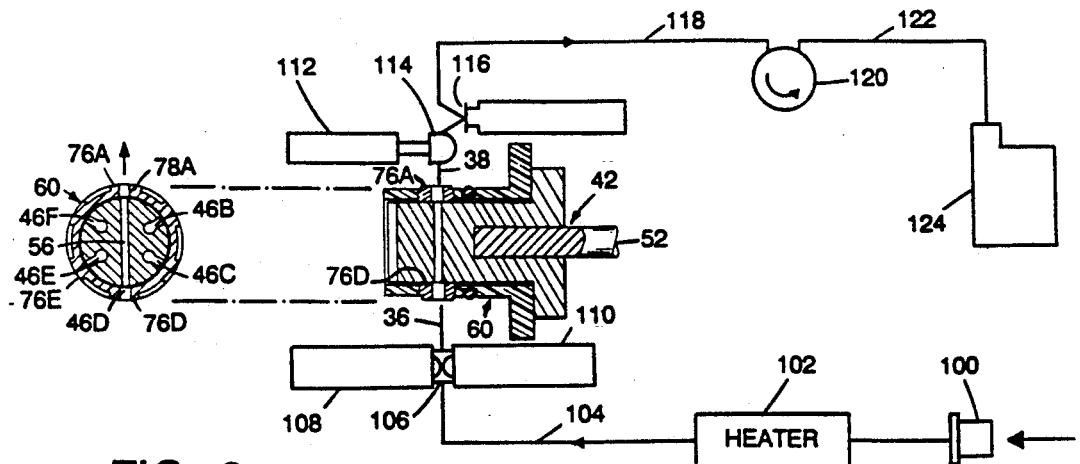
FIGS. 6-8 are diagrammatic views of a blood gas analysis system incorporating the module of FIG. 1 in three different valve positions.

The blood gas analysis module 10 shown in FIG. 1 is of the type disclosed in Weinberg et al., U.S. Pat. No. 4,361,539, the disclosure of which is incorporated herein by reference. That module 10 includes flow through cell 12 fabricated from acrylic plastic and four sleeves 14, 16, 18, 20 of the same material are bonded to the cell body 12 to provide a leak proof unit. A flow through sample path in cell 12 interconnects $PO_2$, pH, $PCO_2$ and reference electrodes which are housed in sleeves 14, 16, 18 and 20, respectively. Within module 10 are aluminum heater blocks 22, 24 which are clamped in heat transfer engagement adjacent corresponding planar surfaces of cell 12 by aluminum plate 26 that has access port 28. Heater blocks 22, 24 carry heater pads and fluid preheater elements. Module 10 is about fifteen centimeters long, about eight centimeters high and about six centimeters deep; and includes a front viewing window, a fiberglass insulating sleeve disposed over the top, rear and bottom walls of the subassembly, and cover structure.

Formed in the rear face of flow through cell member 12 is rectangular recess 30 and cylindrical valve recess 32 of about one centimeter diameter that extends rearwardly from the rear wall of recess 30. In the cylindrical wall of recess 32 is 0.7 millimeter diameter port 34 (FIG. 2) of inlet passage 36 that extends from the $PCO_2$ analysis chamber; and a similar output passage 38 that extends radially outward from oppositely located port 40 in valve recess 32 to the pH analysis chamber.

Disposed within recess 32 is a valve assembly that includes stainless steel spool 42 that is about two centimeters long and about ⅜ centimeter in diameter. In the cylindrical surface 44 of spool 42 are six ports 46A-F (FIG. 3, ports 46A and 46D being connected by 0.7 millimeter diameter through passage 56. Spool member 42 has flange 48 and carries four tubes 50 that extend outwardly from flange 48. Drive shaft 52 is secured in axially extending recess of the valve spool 42 by pin 54.

A valve sleeve component 60 of Delrin includes flange portion 61 and cylindrical portion 62 that has a wall thickness of about one millimeter and formed therein are an annular (about 1.5 millimeters wide and about 0.5 millimeter deep) groove 64 that receives O-ring seal 66; a series of six apertures 68 (each of about 3.5 millimeter diameter) arranged in circumferential array; and an annular recess 70 (about four millimeters wide and about one-half millimeter deep) in the interior of sleeve 60 that receives annular seal member 72.

Seal member 72 is molded of black Viton rubber of 70 Shore A durometer and, as indicated in FIGS. 4 and 5 includes an annular band portion 74 that has a thickness of about 0.6 millimeter and has a width of about four millimeters, a cylindrical inner surface 75 of about eight millimeters diameter, six cylindrical bosses 76A-F each of about 3.5 millimeter diameter and that upstands about one millimeter from the outer surface of annular band portion 72 and opposed passages 78, 80 each of about 1.3 millimeter diameter formed in bosses 76A and 76D, respectively.

In assembly, as indicated in FIG. 2, O-ring seal member 66 is received in groove 64 of sleeve 60; and seal member 72 is disposed in internal groove 70 of sleeve 60 with aligning bosses 76 disposed in apertures 68.

Valve sleeve 60 is inserted into cylindrical recess 32 as indicated in FIG. 2 with seals 66 and 72 in place. In that position, passage 78 of seal 72 is aligned with and sealed to port 40; seal passage 80 is aligned with and sealed to port 34; and O-ring 68 provides an annular seal with the cylindrical surface of recess 32. Valve spool 42 is then inserted into sleeve 60, such that through passage 56 is in axial alignment with seal ports 78, 80, as indicated in FIGS. 2 and 3; and annular seal surface 75 provides a continuous seal with the annular surface of spool 42 adjacent through passage 56. Retainer plate 86 is then disposed in recess 30 and secured with fastener 88 that extends through holes 90 and 92 for threaded securing in recess 94 in cell 12.

A blood gas analysis system that incorporates the valve shown in FIGS. 1-5 is diagrammatically shown in FIG. 6. The blood gas analysis system includes an inlet 100 through which a blood sample is introduced into the system. Inlet 100 is connected to heater 102 which is connected by conduit 104 to analysis chamber 106. Disposed in communication with chamber 106 is a $PO_2$ electrode 108 and a $PCO_2$ electrode 110. The outlet of chamber 106 is connected by passage 36 to valve housing port 34. Valve housing port 40 is connected by passage 38 to capillary measuring chamber 114 of pH electrode 112 and reference junction structure 116. The reference junction is in turn connected by conduit 118 through peristaltic pump 120 and conduit 122 to waste receptacle 124.

In the analysis position of the valve as shown in FIGS. 2, 3 and 6, valve spool 42 is positioned so that ports 46A and 46D of through passage 56 are aligned with seal passages 78 and 80 and sleeve passages 36 and 38; and ports 46B, 46C, 46E and 46F are seated by annular surface 75 of seal 72. In that analysis position, a blood sample of about sixty-five microliter volume is introduced into the measuring chambers of electrodes 108, 110, and 112 and measurements of pH, $PCO_2$ and $PO_2$ are simultaneously obtained on the sample. After the measurements are complete, the sample is flushed from the analysis chambers 106 and 114 and flush solution is drawn through the system in a cleaning operation.

Figure 7:
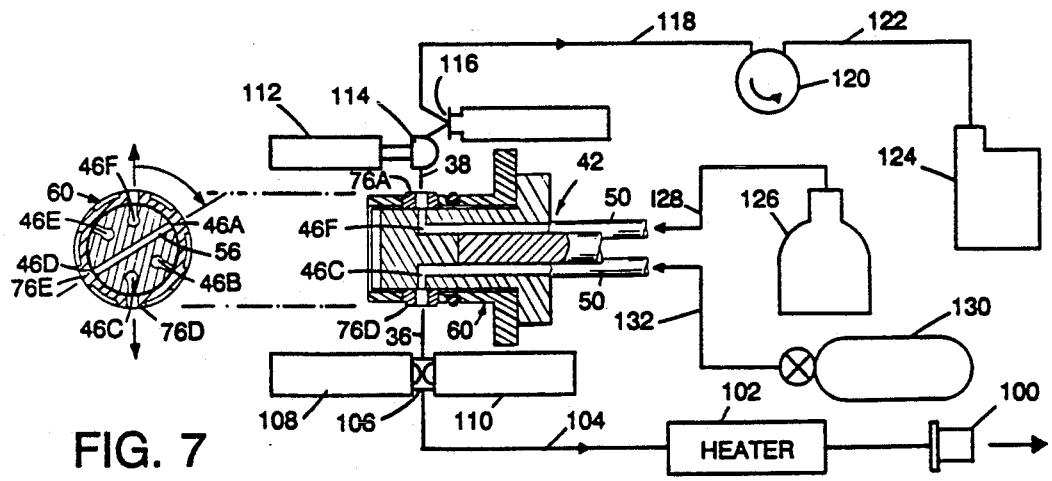
Figure 8:
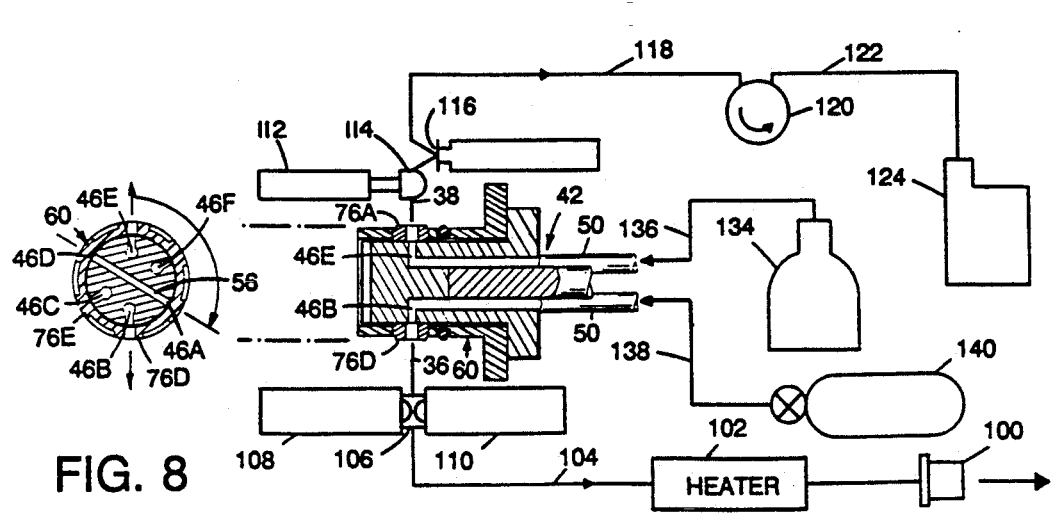

As described in Ambers, U.S. Pat. No. 4,298,026, the electrode system calibration is periodically checked by placing the valve in a calibrate position and allowing a selected calibrated gas to flow in communication with the $PCO_2$ and $PO_2$ electrodes and the pH measuring chamber is connected to a source of buffer liquid. In a first calibrating position shown in FIG. 7, the valve spool 42 is rotated 60° so that port 46F is aligned with housing passage 38 and port 46C is aligned with housing passage 36 (ports 46A, 46B, 46D and 46E being sealed by seal surface 75), in which position a buffer liquid from source 126 is flowed through passage 38 and a calibrating gas from source 130 is flowed through passage 36. In a second calibrating position of the valve spool (shown in FIG. 8), port 46E is aligned with passage 38 (connecting a buffer liquid from source 134 to that passage) and valve port 46E is aligned with passage 36 (connecting a second calibrating gas from source 140 to passage 36) and ports 46A, 46C, 46D and 46F are sealed by seal surface 75. As the valve is moved between the calibrating and analysis positions, the annular inner surface 75 of seal 72 maintains a seal of through passage 56 so that sample material does not leak from passage 56 and flow along the outer surface of the metal spool valve 42. Any tendency to contaminate that surface and interfere with accurate analysis measurements thus is minimized.

While a particular embodiment of the invention has been shown and described, various modifications will be apparent to those skilled in the art, and therefore, it is not intended that the invention be limited to the disclosed embodiment, or to details thereof, and departures may be made therefrom within the spirit and scope of the invention.

What is claimed is:

1. An improved valve for use in an electrochemical analysis system that includes a plurality of flow through analysis chambers, said valve being connected in series between an outlet port of one analysis chamber and an inlet port of a second analysis chamber and having a first position connecting the two analysis chambers in series for flow of a sample to be analyzed therethrough and a second position in which the two analysis chambers are connected to separate sources of calibrating fluids, said valve including a housing member with a cylindrical recess, a valve spool member disposed in said cylindrical recess, said spool member having a cylindrical surface and including a circumferential array of ports in said cylindrical surface, a through passage in said spool member interconnecting two of said ports, and other ones of said ports being separately connected to individual sources of calibrating fluids, said housing and spool members having coaxial cylindrical valve surfaces in juxtaposed spaced relation, a plurality of passages in the housing member, each said passage terminating at a port in said cylindrical housing recess surface, a sleeve member centering said spool member in said housing recess, said sleeve member including a plurality of apertures, and an annular seal member carried by said sleeve member, said seal member having a continuous annular seal surface in sealing engagement with said cylindrical surface of said valve spool member and through passages that are positioned in fixed alignment with ports of said housing member by said sleeve member, and boss portions that protrude through said sleeve apertures for seating against said cylindrical housing recess surface to provide resilient spaced support of said sleeve member in said housing member.

2. The valve of claim 1 wherein said housing member includes a flow through cell, said flow through cell having a flow through sample path that interconnects the two analysis chambers.

3. The valve of claim 2 wherein said housing member recess is of about one centimeter diameter, and said flow through sample path includes an inlet passage that extends from one analysis chamber to a port in the cylindrical wall of said housing recess and an output passage that extends radially outward from an oppositely located port in said housing recess to the other analysis chamber.

4. The valve of claim 1 wherein said spool member includes six ports in said circumferential array of ports, and two oppositely disposed ports are connected by said through passage.

5. The valve of claim 1 wherein said sleeve member has a cylindrical portion with a wall thickness of about one millimeter in which a circumferential array of said sleeve apertures are formed.

6. The valve of claim 1 wherein said sleeve member further includes an annular groove in which an O-ring seal is disposed for sealing engagement with the cylindrical surface of said housing recess.

7. The valve of claim 1 wherein said seal member is molded of elastomeric material of about 70 Shore A durometer and includes an annular band portion of less than one millimeter thickness and less than five millimeters width.

8. An improved valve for use in an electrochemical analysis system that includes a plurality of flow through analysis chambers, said valve being connected in series between an outlet port of one analysis chamber and an inlet port of a second analysis chamber and having a first position connecting the two analysis chambers in series for flow of a sample to be analyzed therethrough and a second position in which the two analysis chambers are connected to separate sources of calibrating fluids, said valve including a housing member with a cylindrical recess, a valve spool member disposed in said cylindrical recess, said spool member having a cylindrical surface and including a circumferential array of ports in said cylindrical surface, a through passage in said spool member interconnecting two of said ports, said spool member including six ports in said circumferential array of ports, and two oppositely disposed of said ports being connected by said through passage, and other ones of said ports being separately connected to individual sources of calibrating fluids, said housing and spool members having coaxial cylindrical valve surfaces in juxtaposed spaced relation, a plurality of passages in the housing member, each said passage terminating at a port in said cylindrical housing recess surface, a sleeve member centering said spool member in said housing recess, said sleeve member including a plurality of apertures, and an annular seal member carried by said sleeve member, said seal member having a continuous annular seal surface in sealing engagement with said cylindrical surface of said valve spool member, six boss portions that protrude through said sleeve apertures for seating against said cylindrical housing recess surface to provide resilient spaced support of said sleeve member in said housing member and each of two oppositely disposed bosses having a through passage that is positioned in fixed alignment with a port of said housing member by said sleeve member.

9. An improved valve for use in an electrochemical analysis system that includes a plurality of flow through analysis chambers, said valve being connected in series between an outlet port of one analysis chamber and an inlet port of a second analysis chamber and ahving a first position connecting the two analysis chambers in series for flow of a sample to be analyzed therethrough and a second position in which the two analysis chambers are connected to separate sources of calibrating fluids, said valve including a housing member with a cylindrical recess, a valve spool member disposed in said cylindrical recess, said spool member having a cylindrical surface and including a circumferential array of ports in said cylindrical surface, a through passage in said spool member interconnecting two of said ports, and other ones of said ports being separately connected to individual sources of calibrating fluids, said housing and spool members having coaxial cylindrical valve surfaces in juxtaposed spaced relation, a plurality of passages in the housing member, each said passage terminating at a port in said cylindrical housing recess surface, a sleeve member centering said spool member in said housing recess, and an annular seal member carried by said sleeve member, said seal member being molded of elastomeric material of about 70 Shore A durometer and including an annular band portion of less than one millimeter thickness and less than five millimeters width and a plurality of outwardly extending boss portions, each said boss portion upstanding about one millimeter from the outer surface of said annular band portion, and through passages in said seal member extending through two of said bosses, said seal member having a continuous annular seal surface in sealing engagement with said cylindrical surface of said valve spool member and said through passages being positioned in fixed alignment with ports of said housing member by said sleeve member.

10. The valve of claim 9 wherein said sleeve member further includes an annular groove in which an O-ring seal is disposed for sealing engagement with the cylindrical surface of said housing recess.

11. The valve of claim 10 wherein said housing member includes a flow through cell, said flow through cell having a flow through sample path that interconnects the two analysis chambers, said housing member recess is of about one centimeter diameter, and said flow through sample path includes an inlet passage that extends from one analysis chamber to a port in the cylindrical wall of said housing recess and an output passage that extends radially outward from an oppositely located port in said housing recess to the other analysis chamber.

12. The valve of claim 11 wherein said sleeve member has a cylindrical portion with a wall thickness of about one millimeter in which a circumferential array of said sleeve apertures are formed.

13. The valve of claim 12 wherein said spool member includes six ports in said circumferential array of ports, and two oppositely disposed ports are connected by said through passage, said seal member includes six boss portions that protrude through said sleeve apertures for seating against said cylindrical housing recess surface to provide resilient spaced support of said sleeve member in said housing member and each of two oppositely disposed bosses has a through passage.

* * * * *